United States Patent

Gerhart et al.

Patent Number: 6,149,642
Date of Patent: Nov. 21, 2000

[54] SURGICAL INSTRUMENT AND METHOD FOR USE IN HAND-ASSISTED LAPAROSCOPY

[75] Inventors: Clark D. Gerhart, Hazleton; Robert D. Rambo, Sellersville, both of Pa.

[73] Assignee: Medical Creative Technologies Inc., Colmar, Pa.

[21] Appl. No.: 09/008,135

[22] Filed: Jan. 16, 1998

[51] Int. Cl.⁷ ..................................................... A61B 17/00
[52] U.S. Cl. .............................. 606/1; 606/210; 128/897
[58] Field of Search ....................... 606/1, 210; 128/897

[56] References Cited

U.S. PATENT DOCUMENTS

| | | |
|---|---|---|
| 4,374,523 | 2/1983 | Yoon . |
| 5,263,927 | 11/1993 | Shlain . |
| 5,295,952 | 3/1994 | Pietrafitta . |
| 5,304,187 | 4/1994 | Green . |
| 5,324,304 | 6/1994 | Rasmussen . |
| 5,417,708 | 5/1995 | Hall et al. . |
| 5,503,623 | 4/1996 | Tilton et al. . |
| 5,514,084 | 5/1996 | Fisher . |
| 5,524,644 | 6/1996 | Crook . |
| 5,556,376 | 9/1996 | Yoon . |
| 5,640,977 | 6/1997 | Leahy et al. . |

*Primary Examiner*—Michael H. Thaler
*Attorney, Agent, or Firm*—Howson & Howson

[57] ABSTRACT

A surgical instrument and the method for delivering and withdrawing surgical tools through a cannula in an abdominal cavity during hand-assisted minimally invasive surgery. A tube slidably extends through a cannula with a slender surgical tool such as a suture needle holder, secured in a snap-in gripper at the insertion end of the tube. The thumb and fingers of one hand of the surgeon or an assistant's cause the tube to move axially from a fully retracted position in the cannula to a position where the tool projects from a snap-in socket in the tube a length sufficient for a surgeon's hand to grip a knurled surface around the tool. A detent bead around the periphery of the tool snaps into a complementary groove within the gripper. Insufflating gas may be introduced or vented as needed through a port which communicates through the interior of the tube with the abdominal cavity. The procedure is reversed for withdrawing the tool.

15 Claims, 2 Drawing Sheets

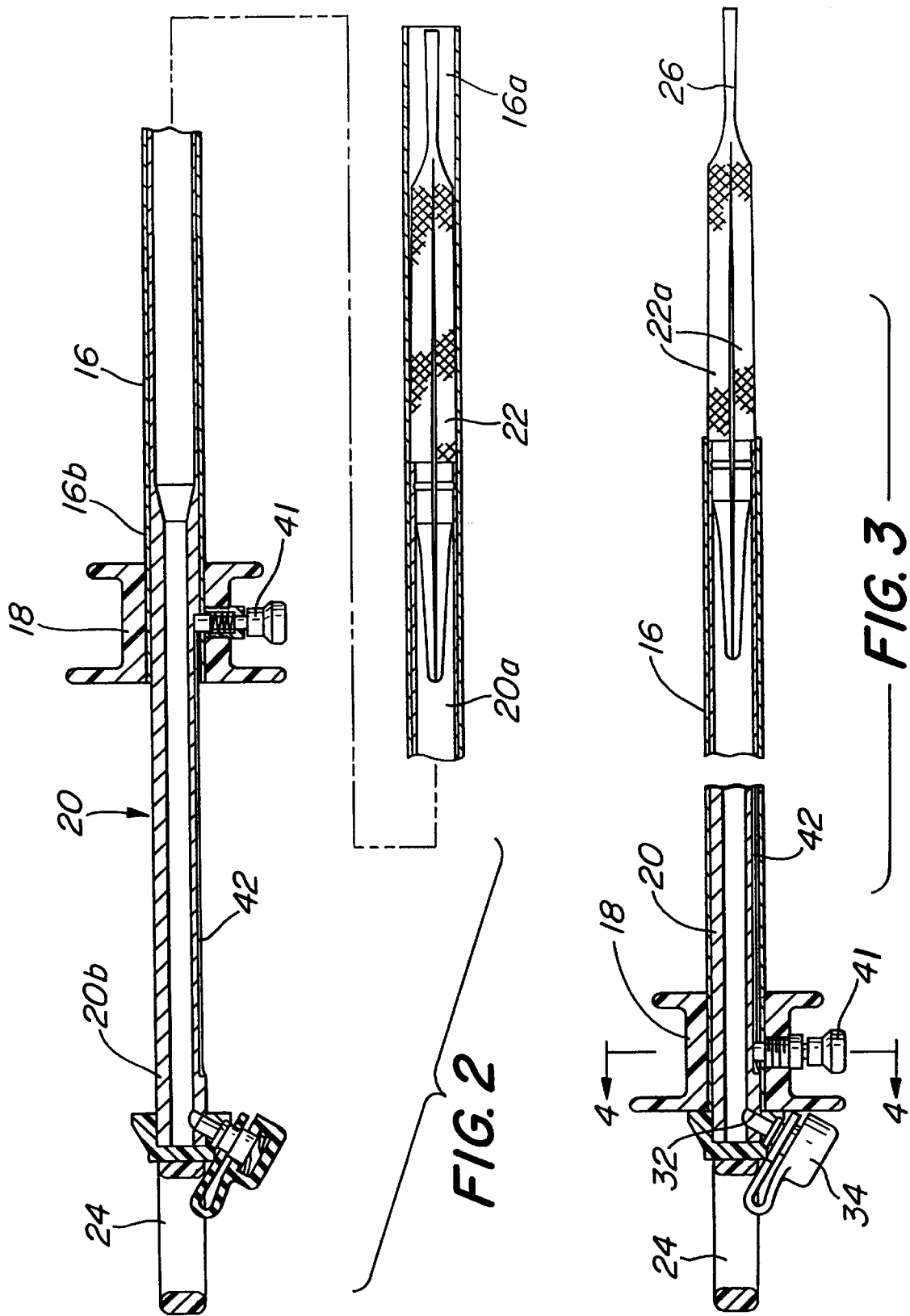

SURGICAL INSTRUMENT AND METHOD FOR USE IN HAND-ASSISTED LAPAROSCOPY

FIELD OF THE INVENTION

The present invention relates generally to apparatus for use in surgery, and more particularly to apparatus suitable for either delivering surgical tools to a surgeon's hand within an abdominal cavity of a patient or removing them from the hand during laparoscope procedures.

BACKGROUND OF THE INVENTION

Laparoscopy, also referred to as keyhole surgery, is a relatively recent minimal invasive surgical technique in which instruments such as miniature lights, cameras and surgical tools are inserted into an insufflated abdominal cavity through a small incision or puncture wound and manipulated externally with the aid of an endoscope and TV monitor. Considerable skill and experience is generally required to position the instruments spatially relative to internal organs viewed on a two-dimensional monitor.

A modified laparoscopic technique has evolved which is referred to as hand-assisted minimally invasive surgery in which one hand of the surgeon has access to the cavity while maintaining pneumoperitoneum. This technique, such as described in U.S. Pat. No. 5,640,977 to Patrick F. Leahy, et al. is now an alternative procedure of choice where conditions allow. For the patient, trauma is minimized, the risk of damage to the immune system is reduced, and healing time and length of stay in hospital are both shortened because only a relatively small additional incision is required just sufficient for admitting the surgeon's hand. For the surgeon, less training is required because the presence of his/her hand in the cavity allows palpation of internal organs, biophysical feedback, and easier manipulation of various instruments from within the cavity while viewing the TV monitor. However, during a surgical procedure more than one surgical tool may be required but is too difficult to hold onto while another is manipulated within the cavity. Instead, the surgeon must withdraw the hand from the cavity in order to change to another tool, consequently interrupting the procedure and disturbing pneumoperitoneum.

SUMMARY OF THE INVENTION

Accordingly, it is an object of the present invention to provide a novel instrument for delivering and withdrawing surgical tools in an insufflated abdominal cavity during hand-assisted minimally invasive laparoscopic surgery.

Another object of the invention is to provide a surgical instrument for changing surgical tools within a sufflated abdominal cavity without disturbing pneumoperitoneum.

Still another object of the invention is to provide a method for transferring surgical tools through a cannula to an abdominal cavity during hand-assisted minimally invasive surgery.

A further object of the invention is to provide a method for use in hand-assisted minimally invasive surgery in which surgical devices can be readily delivered into an abdominal cavity, detached for use, and reattached for withdrawal by one hand held in the cavity.

Still another object is to provide an instrument for transferring a surgical tool either into or out of an abdominal cavity which instrument is simple in construction and easy to use.

These and other objects and novel features of the invention are accomplished by an instrument comprising a slender cannula with a distal end insertable in a patient's abdomen through a small incision or puncture wound. A handle, fixed around the proximal end of the cannula, is formed to be held between the fingers of one hand of the surgeon or an assistant for externally manipulating the distal end in the abdomen. A tube slidably extends through the cannula with a slender surgical tool, such as a suturing needle holder, secured in a snap-in socket at the distal or insertion end of the tube. A ring handle formed to receive the thumb of the one hand is fixed to the proximal end and seals the adjacent end opening of the tube. A port with a removable cap communicates through the ring with the tube interior for introducing, sealing or venting sufflating gas in the cavity.

Axial movement of the tube in the cannula is limited by a spring-biased pin extending through the side of the cannula into a slot along the length of the tube from one extreme position where the tool is completely within the cannula to where the tool projects from the snap-in socket a length sufficient for a surgeon's hand to grip a knurled section around the tool. A resilient bifurcated portion of the tool has a circumferential bead or detent around the periphery which snaps into a complementary groove within the socket when the tip of the bifurcated portion is squeezed together.

Operating under conditions of hand-assisted laparoscopy, when the surgeon requires a tool delivered to the hand in the abdominal cavity, the finger grip and ring are spread apart by another externally located hand to completely retract the tool in the cannula. The instrument is inserted through a small incision or puncture wound. Sliding the grip and ring together, the knurled section of the tool exposes it at the tube socket for grasping and removing by the surgeon's hand. After use, the tool is retrieved from the cavity by snapping it back into the socket and retracting the tube and cannula in reverse order.

BRIEF DESCRIPTION OF THE DRAWINGS

The foregoing and other objects, novel features and advantages of the invention will become more apparent from the following description when taken in conjunction with the accompanying drawings wherein:

FIG. 2 is a longitudinal view partially in cross section of the instrument of FIG. 1 with the needle holder fully retracted in the cannula;

FIG. 3 is a longitudinal view partially in cross section of the instrument of FIG. 1 with a knurled section of the needle holder fully exposed from the cannula for gripping by a surgeon's hand;

DESCRIPTION OF A PREFERRED EMBODIMENT

Figure 1:
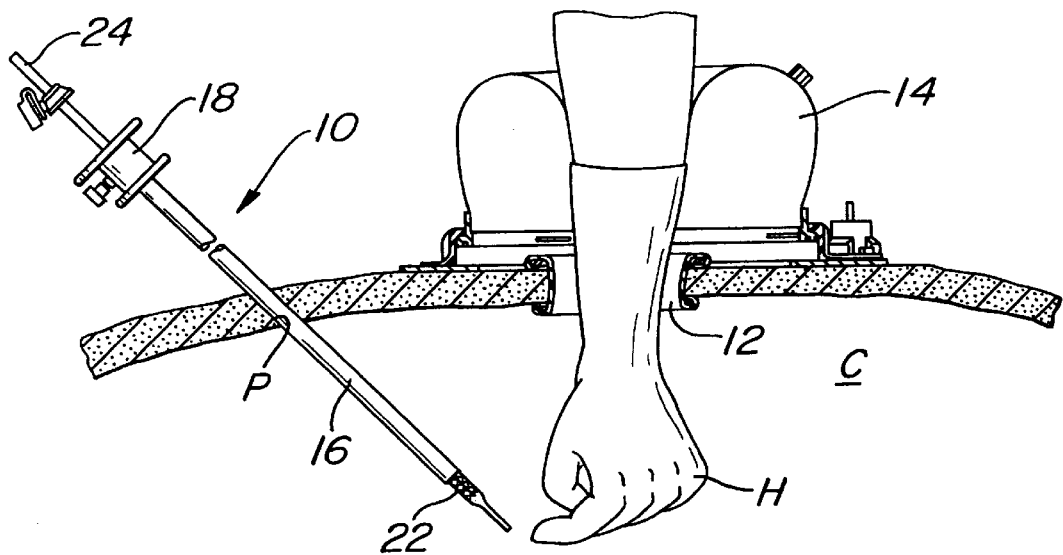
FIG. 1 is a schematic representation of a surgical instrument according to the invention in which a suture needle holder partially extends from a cannula inserted in a sufflated abdominal cavity during hand-assisted surgery.

Referring now to the drawings wherein like reference characters and numbers designate like or corresponding parts throughout the several views, there is shown in FIG. 1 a preferred embodiment of a surgical instrument 10 according to the invention for delivering and removing tools during a hand-assisted laparoscopy. Instrument 10 is inserted through a puncture wound P into a sufflated abdominal cavity C with its distal end positioned within easy reach of a surgeon's hand H which has been extended through a wound retractor 12 installed in a small incision such as described in U.S. Pat. No. 08/5,524,644 to Berwyn M. Crook. A flexible enclosure 14 sealed around the incision and the hand H prevents loss of pneumoperitoneum while allowing the surgeon freedom of movement within cavity C. An enclosure suitable for this purpose is described in U.S. patent application Ser. No. 08/801,752, now U.S. Pat. No. 5,853,395, filed Feb. 18, 1997. However, other similar types of retractors and enclosures may be used without departing from the invention as claimed herein.

Figure 4:
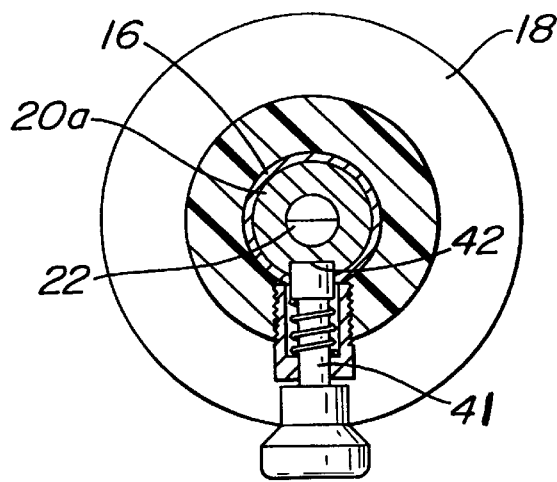
FIG. 4 is a transverse view in cross section of the instrument taken in a plane along the line 4—4 in FIG. 3.

Referring to the more detailed drawings of FIGS. 2–4, instrument 10 comprises a straight slender cannula 16, made of thin gauge metal such as a surgical stainless steel, having a distal end 16a insertable through puncture wound P in the abdomen, and a proximal end 16b supporting a plastic finger grip 18. An annular groove in finger grip 18 is formed to receive adjacent fingers of one hand for externally manipulating instrument 10, with the aid of an endoscope and TV monitor (not shown), into a position accessible to a surgeon's hand within cavity C. A tube 20 preferably of surgical stainless steel slides lengthwise in cannula 16 and defines a distal end 20a which carries a surgical tool, such as a sterile tweezer, or suturing needle holder, 22, or the like. A plastic ring 24 mounted on a proximal end 20b of tube 20 is formed to receive the thumb and seal the adjacent tube end opening.

Figure 5:
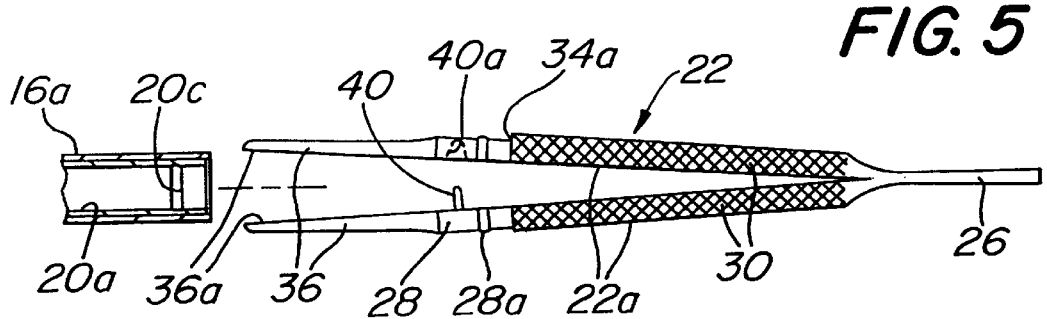
FIG. 5 is a side view of the needle holder with jaws of the holder in a normally open position.

Referring to FIG. 5, tool 22 is bifurcated from a stem 26 at one end into a pair of normally open members 22a defining a detent section 28 between stem 26 and an externally knurled, or anti-slip, surface 30 for gripping tool 22. Members 22a terminate in tapered jaws 36 with serrated tips 36a for gripping a suture needle or like device. When members 22a are squeezed together for insertion within tube 20, jaws 36 close with detent section 28 urged against the inner surface of tube 20 and knurled surface 30 is slidable within the entire length of cannula distal end 16a. A shoulder 34a formed at the junction of detent section 28 and knurled section 30 limits the insertion of tool 22 in tube 20, and a circumferential bead 28a in section 28 seats in a complementary groove, or gripper, 20c within tube 20 to provide a snap-in interference fit with tool 22. Jaws 36 self-align in the closed state by a pin 40 extending from one member 22 through a tapered hole 40a in the opposite member 22. While the illustrated gripper engages externally of the surgical tool, it should be apparent that a gripper that engages interiorly of a surgical tool may be employed with like effect and equivalent function.

While instrument 10 is in use, insufflating gas may be introduced or vented as needed through a port 32 which communicates through thumb grip 24 with the interior of tube 20. A removable elastic cap 34 seals port 32 against loss of gas pressure. Generally, however, the port 32 will be used primarily for cleaning and sterilizing the tube 20.

Tube 20 is slidable in and out of cannula 16 by applying opposite forces to finger grip 18 and ring 24 by the one hand externally manipulating instrument 10. The amount of travel is limited by a spring-biased pin 41 mounted in finger grip 18 and slidably extending through cannula 16 into a slot 42 in the tube proximal end 20b. The wall thickness along the distal end 20b of tube 20 is preferably of thin gauge steel, but is made thicker along the proximal end 20a in order to accommodate the depth of slot 28. The length of slot 42 allows holder 22 to move from a fully retracted position in cannula 16 (FIG. 2) to a position where knurled surface 30 is fully exposed for gripping (FIG. 3).

In use, the surgeon or an assistant places the thumb of one hand through ring 28 and the fingers around finger grip 18 and closes them. Tube 20 slides from the position shown in FIG. 2 where pin 41 is at the distal end of slot 42 to the proximal end of slot 36 thereby extending tool 22 to the exposed position for access by the surgeon's hand within the abdominal cavity. The surgeon then applies a slight pulling force on the exposed knurled surface 30 to release the device for use in a surgical procedure. When completed, the device is snapped back into the socket and the tube retracted into the cannula.

As used herein, the term tool includes, but is not limited to: biopsy, disecting, grasping and holding forceps; Debakey intestinal forceps; scissors; punches; occlusion clamps; and sutures. Also, while reference is made to insertion and withdrawal of the same tool, it should be apparent that the method and apparatus of the present invention contemplates situations wherein one or more tools may be carried into the body by a surgeon, and the apparatus used simply to extract one or more tools during the course of the surgery simply by attaching the tool in the tube gripper, retracting the tube in the cannula, and withdrawing the cannula.

Some of the many advantages and novel features of the invention as described should now be readily apparent. For instance, a surgical instrument is provided in which a miniature surgical tool can be readily delivered into an abdominal cavity, detached for use, and reattached for withdrawal by one hand held in the cavity. The instrument is particularly applicable in hand-assisted minimally invasive surgery under conditions of pneumoperitoneum. The design and construction are relatively simple and easy to use.

It will be understood, of course, that various changes in the details, materials, steps and arrangement of parts, which have been herein described and illustrated in order to explain the nature of the invention, may be made by those skilled in the art within the principle and scope of the invention as expressed in the claim appended hereto.

We claim:

1. Apparatus for use in hand-assisted laparoscopy in which one hand of a surgeon is inserted in an insufflated abdominal cavity, comprising:

a cannula having a distal end portion insertable through a puncture wound into the cavity, and a proximal end portion with a finger grip affixed thereto;

a tube slidable lengthwise in said cannula having a thumb grip sealing one end of said tube adjacent to said proximal end portion, and a gripper formed in said tube near an opposite end thereof;

a surgical tool having members insertable in said gripper when said members are squeezed together; and limit means connected between said cannula and said tube for limiting travel of the tool between a retracted position within said distal end portion and a partially extended position sufficient for the one hand to grasp and release said tool from said gripper for use by the surgeon within the cavity.

2. Apparatus according to claim 1 further comprising:

detent means operatively connected to said gripper and said tool for producing a snap-in fitting.

3. Apparatus according to claim 2 wherein said detent means further comprises:

a circumferential groove within said gripper providing a socket; and a circumferential bead around said tool mating with said groove in an interference fit.

4. Apparatus according to claim 1 wherein said limit means comprises:
 a slot along the external surface of said tube adjacent to said proximal end, the length of said slot being equal to said selected exposure length; and
 a pin projecting from said cannula into said slot, said pin positioned in said cannula to limit travel of said tube in said slot.

5. Apparatus according to claim 5 wherein said limit means further comprises:
 force-exerting means for urging said pin into said slot.

6. Apparatus according to claim 1 further comprising:
 a circumfrential groove in said gripper; and
 a circumferential bead around said tool mating with said groove for producing an interference fit.

7. Apparatus according to claim 1 further comprising:
 a knurled surface around said members for enabling positive finger gripping of the tool.

8. Apparatus according to claim 1 further comprising:
 alignment means operatively connected between said jaw members for aligning the said members when squeezed together.

9. A method for delivering a surgical tool to a surgeon's hand within an insufflated abdominal cavity comprising the steps of:
 inserting one end of a slender surgical tool axially into a snap-in gripper at a distal end of an elongate tube;
 sliding the tube in a cannula until the tool is completely withdrawn in a distal end of the cannula;
 inserting the distal end of the cannula through a wound in the abdomen to within easy reach of the surgeon's hand;
 sliding the tool forwardly through the cannula until the tool is sufficiently exposed for the surgeon's hand to grasp; and
 removing the tool from the gripper within the cavity for executing a surgical procedure.

10. A method according to claim 9 further comprising to steps of:
 reinserting the tool in the gripper;
 retracting the tube in said cannula until the tool is completely inside the cannula; and
 withdrawing the cannula from the cavity.

11. In a surgical instrument for hand-assisted minimally invasive surgery within a body cavity under conditions of pneumoperitoneum, the combination comprising:
 an elongate outer tube having a forward end and a rearward end, a first handle at the rearward end formed to be gripped by the fingers of one hand;
 an inner tube slidable in said outer tube having a forward end and a rearward formed to be gripped by the thumb of the one hand;
 tool means operably and removably carried at the inner tube forward end, said tool means including opposed first and second ends, said first end having a cross sectional area slidable into said forward end of said inner tube and a second end retractable into said outer tube; and
 interference fitting means operatively connecting said first end of said tool means to said inner tube forward end, including a circumferential bead around said tool means mating with a circumferential groove around the interior of said inner tube.

12. An instrument according to claim 11 wherein said tool means comprises a bifurcated shaft having normally open jaws compressed together to fit in the forward end of said inner member.

13. An instrument according to claim 11 including a reclosable port in said cannula.

14. A method for withdrawing a surgical tool from a surbon's hand within an insufflated abdominal cavity comprising the steps of:
 inserting the distal end of a cannula through a wound in the abdomen to within easy reach of the surgeon's hand;
 inserting one end of the surgical tool into a snap-in gripper at a distal end of an elongate tube;
 retracting the tube in the cannula until the tool is completely withdrawn into the cannula; and
 withdrawing the cannula and hence the tool from the abdominal cavity.

15. A method for delivering a surgical tool to a surgeon's hand within an insufflated abdominal cavity, comprising the steps of:
 inserting one end of a tool axially into a snap-in gripper at a distal end of a tube sidable within a cannula with the tool contained within a distal end portion of the cannula;
 inserting the distal end portion of the cannula with the distal end of the tube through a wound in the abdomen within easy reach of the surgeon's hand; and
 sliding the tube toward the distal end of the cannula to expose a distal portion of the tool for grasping by the surgeon.

* * * * *